United States Patent [19]

Kiyasu et al.

[11] Patent Number: 5,440,649
[45] Date of Patent: Aug. 8, 1995

[54] METHOD OF AND APPARATUS FOR INSPECTION OF EXTERNAL APPEARANCE OF A CIRCUIT SUBSTRATE, AND FOR DISPLAYING ABNORMALITY INFORMATION THEREOF

[75] Inventors: Senya Kiyasu, Yokohama; Takanori Ninomiya, Hiratsuka, both of Japan

[73] Assignee: Hitachi, Ltd., Tokyo, Japan

[21] Appl. No.: 930,346

[22] Filed: Aug. 17, 1992

Related U.S. Application Data

[62] Division of Ser. No. 668,022, Mar. 12, 1991.

[30] Foreign Application Priority Data

Mar. 14, 1990 [JP] Japan ............... 2-060961
Apr. 25, 1990 [JP] Japan ............... 2-107564
Aug. 1, 1990 [JP] Japan ............... 2-202441

[51] Int. Cl.⁶ ............................................. G06K 9/62
[52] U.S. Cl. ............................................. 382/147
[58] Field of Search ................. 382/8, 26, 69, 28; 358/106, 125

[56] References Cited

U.S. PATENT DOCUMENTS

| | | | |
|---|---|---|---|
| 3,751,647 | 8/1973 | Maeder et al. | 382/8 |
| 4,519,041 | 5/1985 | Fant et al. | 382/22 |
| 4,587,617 | 5/1986 | Barker et al. | 358/106 |
| 4,659,220 | 4/1987 | Bronte et al. | 382/8 |
| 4,809,308 | 2/1989 | Adams et al. | 382/8 |
| 4,845,558 | 7/1989 | Tsai et al. | 358/106 |
| 4,896,278 | 1/1990 | Grove | 73/598 |
| 4,910,411 | 3/1990 | Teraguchi et al. | 358/106 |
| 5,093,797 | 3/1992 | Yotsuya et al. | 382/8 |

*Primary Examiner*—David K. Moore
*Attorney, Agent, or Firm*—Fay, Sharpe, Beall, Fagan, Minnich & McKee

[57] ABSTRACT

An apparatus for visual inspection detects defects on an object to be inspected, stores the defects, calculates the distance between two detected defects from the positions of the two detected defects, and judges the two detected defects to be different portions of a single actual defect when the distance between the two defects is less than a predetermined threshold value. The apparatus also stores the actual defects, as well as class-of-actual-defect inference rules necessary for inferring the class of the actual defects from the class of each detected defect. The class of the actual defect is judged from the class of each detected defect on the basis of the class-of-actual-defect inference rules, and the class of the actual defect is then stored. A method of visual inspection and a method of removing the cause of an abnormality are also disclosed.

11 Claims, 8 Drawing Sheets

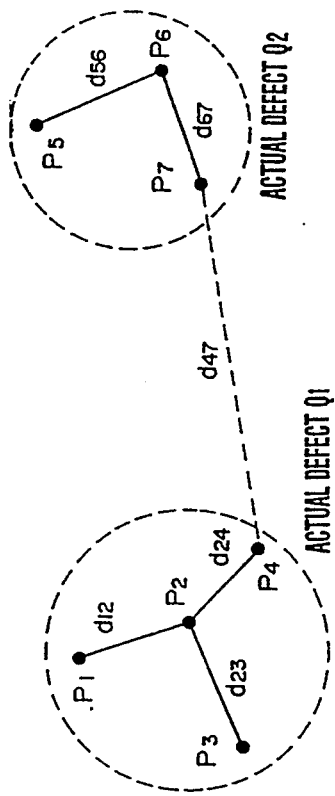

| RULE NO. | PRESUMPTION RULE OF KIND OF ACTUAL DEFECT | | |
|---|---|---|---|
| | CONDITION | | PRESUMED KIND |
| 1 | if | (THE NUMBER OF BLUR DEFECTS > 0<br>THE NUMBER OF SCATTERING DEFECTS > 0<br>THE NUMBER OF ISOLATED POINT DEFECTS > 0) | then (STICKING OF PASTE OR DUST ON GREEN SHEET) |
| 2 | if | (THE NUMBER OF BLUR DEFECTS > 0<br>THE NUMBER OF OTHER DEFECTS=0) | then (BLUR OF PASTE) |
| 3 | if | (THE NUMBER OF BLUR DEFECTS > 0<br>THE NUMBER OF DEFICIENCY DEFECTS > 0) | then (STICKING OF DUST ON GREEN SHEET) |
| ... | | | |

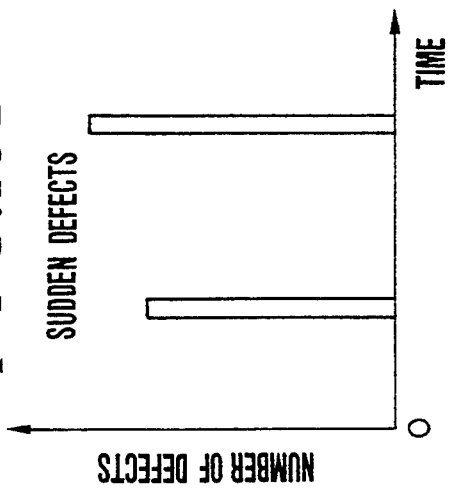
FIG.10B SUDDEN DEFECTS
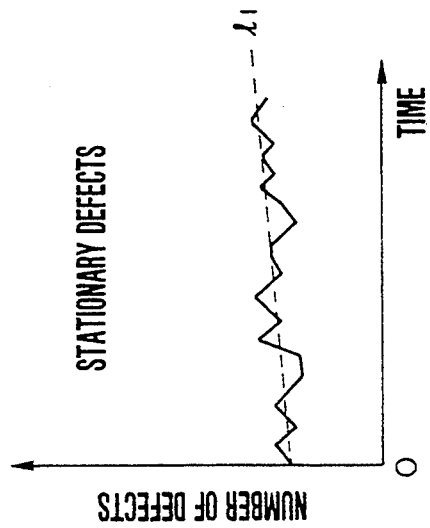
FIG.10C STATIONARY DEFECTS
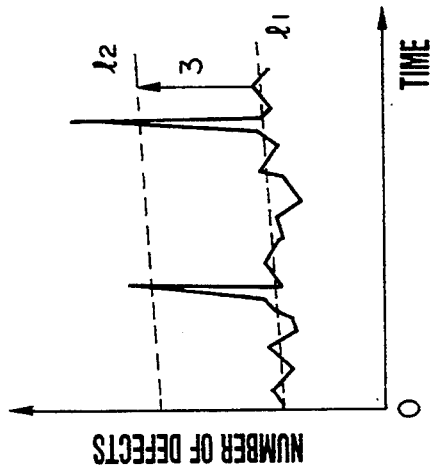
FIG.10A

FIG. 11

| ABNORMALITY JUDGEMENT RULE ||| 
|---|---|---|
| RULE No. | CONDITION | JUDGEMENT OF ABNORMALITY |
| 1 | if $(\overline{x^2+y^2})$ > REFERENCE $T_0$<br>$(\overline{x},\overline{y})$ : BARYCENTER OF DISTRIBUTION OF DEFECTS | then DEFECTS ARE DISTRIBUTED MAINLY ON ONE SIDE<br>$X_1$: ABNORMALITY |
| 2 | if $\sigma^2$ < REFERENCE $T_1$<br>$\sigma^2$: VARIANCE OF DISTRIBUTION OF DEFECTS | then DEFECTS ARE LOCALIZED<br>$X_2$: ABNORMALITY |
| 3 | if b > REFERENCE $T_2$<br>b: INCREASE RATE OF NUMBER OF DEFECTS | then THE NUMBER OF DEFECTS INCREASES<br>$X_3$: ABNORMALITY |

FIG. 12

| PRESUMPTION RULE OF CAUSE OF ABNORMALITY |||
|---|---|---|
| RULE No. | CONDITION | PRESUMED CAUSE OF ABNORMALITY |
| 1 | if BLUR DEFECTS<br>MANY STATIONARY DEFECTS<br>UNIFORM DISTRIBUTION | then THERE IS POSSIBILITY OF INAPPROPRIATE VISCOSITY OF PASTE<br>$Y_1$: CONVICTION VALUE |
| 2 | if SCATTERING OF PASTE<br>MANY STATIONARY DFECTS<br>UNIFORM DISTRIBUTION | then THERE IS POSSIBILITY OF INAPPROPRIATE VISCOSITY OF PASTE<br>$Y_2$: CONVICTION VALUE |

METHOD OF AND APPARATUS FOR INSPECTION OF EXTERNAL APPEARANCE OF A CIRCUIT SUBSTRATE, AND FOR DISPLAYING ABNORMALITY INFORMATION THEREOF

This application is a divisional of application Ser. No. 07/668,022, filed Mar. 12, 1991.

BACKGROUND OF THE INVENTION

The present invention relates to not only a method of and an apparatus for visual inspection but also a method of removing the cause of abnormality.

In order to maintain or improve the manufacturing yield and quality of products in the manufacturing process thereof, it is necessary to keep the manufacturing process at a favorable state. When an abnormality is generated in the manufacturing process, it is required to detect the abnormality quickly, to clear up the cause of the abnormality, and to take an appropriate countermeasure. Accordingly, abnormalities in a manufacturing process have been detected as shown in the paper entitled "Knowledge-Based Process Diagnosis Method for Semiconductor Manufacturing" (Transactions of Information Processing Society of Japan) Vol. 27, No. 5, pages 541 to 551) and Japanese patent applications laid-open No. JP-A-60-257,535 and JP-A-62-98,739.

A method of and an apparatus for visual inspection can be used for detecting an abnormality in a manufacturing process. When an abnormality is generated in the manufacturing process, a defect is produced on an object to be inspected, or a foreign particle adheres to the object (such a foreign particle will hereinafter be also referred to as a "defect"). Thus, the appearance of the to-be-inspected object is varied. That is, the abnormality in the manufacturing process can be detected by inspecting the appearance of the object.

According to a method of and an apparatus for visual inspection, however, actual defects do not always exist on a one-to-one basis for detected defects. Accordingly, it has been impossible to accurately judge an abnormality in the manufacturing process, and to remove the cause of abnormality surely. Thus, it has been impossible to maintain or improve the manufacturing yield and quality of an article.

SUMMARY OF THE INVENTION

It is an object of the present invention to provide a method of and an apparatus for visual inspection, and also a method of removing the cause of an abnormality, for accurately judging that an abnormality exists in a manufacturing process and for surely removing the cause of abnormality.

In order to attain the above object, according to an aspect of the present invention, there is provided a method of visual inspection which comprises the steps of: detecting defects on an object to be inspected; calculating the distance between two of the detected defects from the positions of the detected defects; judging the two detected defects to be different portions of a single actual defect when the distance between two detected defects is less than a predetermined threshold value; and judging the class of the actual defect on the basis of predetermined, class-of-actual-defect inference rules.

Further, according to another aspect of the present invention, there is provided another method of visual inspection which comprises the steps of: detecting defects on an object to be inspected; extracting actual defects from detected defects; obtaining a feature parameter indicative of at least one of the variation of the number of actual defects with time and the two-dimensional distribution of actual defects; and judging that an abnormality exists on the basis of abnormality judgement rules for correlating the feature parameters with the presence of an abnormality in a manufacturing process.

In this method, it is preferable to calculate the distance between two of the detected defects from the positions of the two detected defects, to judge the two detected defects to be different portions of a single actual defect when the distance between two detected defects is less than a predetermined threshold value, and to judge the class of the actual defect on the basis of a predetermined, class-of-actual-defect inference rule.

According to a further aspect of the present invention, there is provided an apparatus for visual inspection which comprises: defect detection means for detecting defects on an object to be inspected; detected defect storage means for storing the data of defects which are detected by the defect detection means; actual defect extraction means for calculating the distance between two of the detected defects from the positions of the two detected defects and for judging the two detected defects to be different portions of a single actual defect when the distance between the two detected defects is less than a predetermined threshold value; actual defect storage means for storing the data of actual defects which are extracted by the actual defect extraction means; an actual defect inference knowledge base for storing class-of-actual-defect inference rules necessary for inferring the class of an actual defect from the class of each detected defect; class-of-defect inference means for judging the class of the actual defect from the class of each detected defect on the basis of the class-of-actual-defect inference rules stored in the actual defect inference knowledge base; and actual defect storage means for storing the class of the actual defect.

Further, according to still another aspect of the present invention, there is provided an apparatus for visual inspection which comprises: defect detection means for detecting defects on an object to be inspected; detected defect storage means for storing the data of the defects which are detected by the defect detection means; actual defect extraction means for extracting actual defects from detected defects; actual defect storage means for storing the data of the actual defects; feature parameter calculation means for obtaining feature parameters indicative of at least one of the variation of the number of actual defects with time and the two-dimensional distribution of actual defects; an abnormality judgment knowledge base for storing abnormality judgment rules necessary for correlating the feature parameters with the presence of abnormality in a manufacturing process; and abnormality judgment means for judging the abnormality in the manufacturing process from the feature parameters, on the basis of the abnormality judgment rules stored in the abnormality judgment knowledge base.

In this apparatus, it is preferable that means for calculating the distance between two of the detected defects from the positions of the two detected defects and for judging the two detected defects to be different portions of a single actual defect when the distance between the two detected defects is less than a predetermined threshold value, is used as the actual defect extraction means, and that the apparatus further comprises an actual defect inference knowledge base for storing a class-of-actual-defect inference rules necessary for inferring the class of an actual defect from the class of each detected defect, and class-of-defect inference means for judging the class of the actual defect from the class of each detected defect on the basis of the class-of-actual-defect inference rules stored in the actual defect inference knowledge base.

According to still a further aspect of the present invention, there is provided a method of removing the cause of an abnormality which comprises the steps of: detecting defects on an object to be inspected; extracting actual defects from the detected defects; obtaining feature parameters indicative of at least one of the variation of the number of actual defects with time and the two-dimensional distribution of actual defects; judging an abnormality by abnormality judgment rules for correlating the feature parameters with the presence of an abnormality in a manufacturing process; infering the cause of the abnormality on the basis of cause-of-abnormality inference rules indicative of a causal relation between the feature parameters and the cause of the abnormality; and removing the cause of the abnormality in the manufacturing process, on the basis of the abnormality judged by the abnormality judgment rules and the inferred cause of abnormality.

In this method, it is preferable to calculate the distance between two of the detected defects from the positions of the two detected defects, to judge two detected defects to be different portions of a single actual defect when the distance between two detected defects is less than a predetermined threshold value, and to judge the class of the actual defect on the basis of a predetermined, class-of-actual-defect inference rules.

According to the method of and the apparatus for visual inspection and the method of removing the cause of abnormality, an abnormality in a manufacturing process can be rightly judged, and the cause of abnormality can be surely removed.

As is evident from the above, according to an inventive method of visual inspection, an inventive apparatus for visual inspection, and an inventive method of removing the cause of abnormality, an abnormality in a manufacturing process can be rightly judged, and the cause of abnormality can be surely removed. Thus, the present invention can exhibit a remarkable effect that the manufacturing yield and quality of an article can be surely maintained or improved.

BRIEF DESCRIPTION OF THE DRAWINGS

FIG. 8 is a schematic diagram showing a positional relation among detected defects and the distance between two of the detected defects.

FIG. 9 is a table showing class-of-actual-defect inference rules stored in the actual defect inference knowledge base of FIG. 1.

FIGS. 10A to 10C are graphs for explaining a method of obtaining a feature parameter which indicates the variation of the number of actual defects with time, by means of the feature parameter calculation means of FIG. 1.

FIG. 11 is a table showing abnormality judgment rules stored in the abnormality judgment knowledge base of FIG. 1.

FIG. 12 is a table showing cause-of-abnormality inference rules stored in the cause-of-abnormality inference knowledge base of FIG. 1.

DESCRIPTION OF THE PREFERRED EMBODIMENTS

Figure 1:
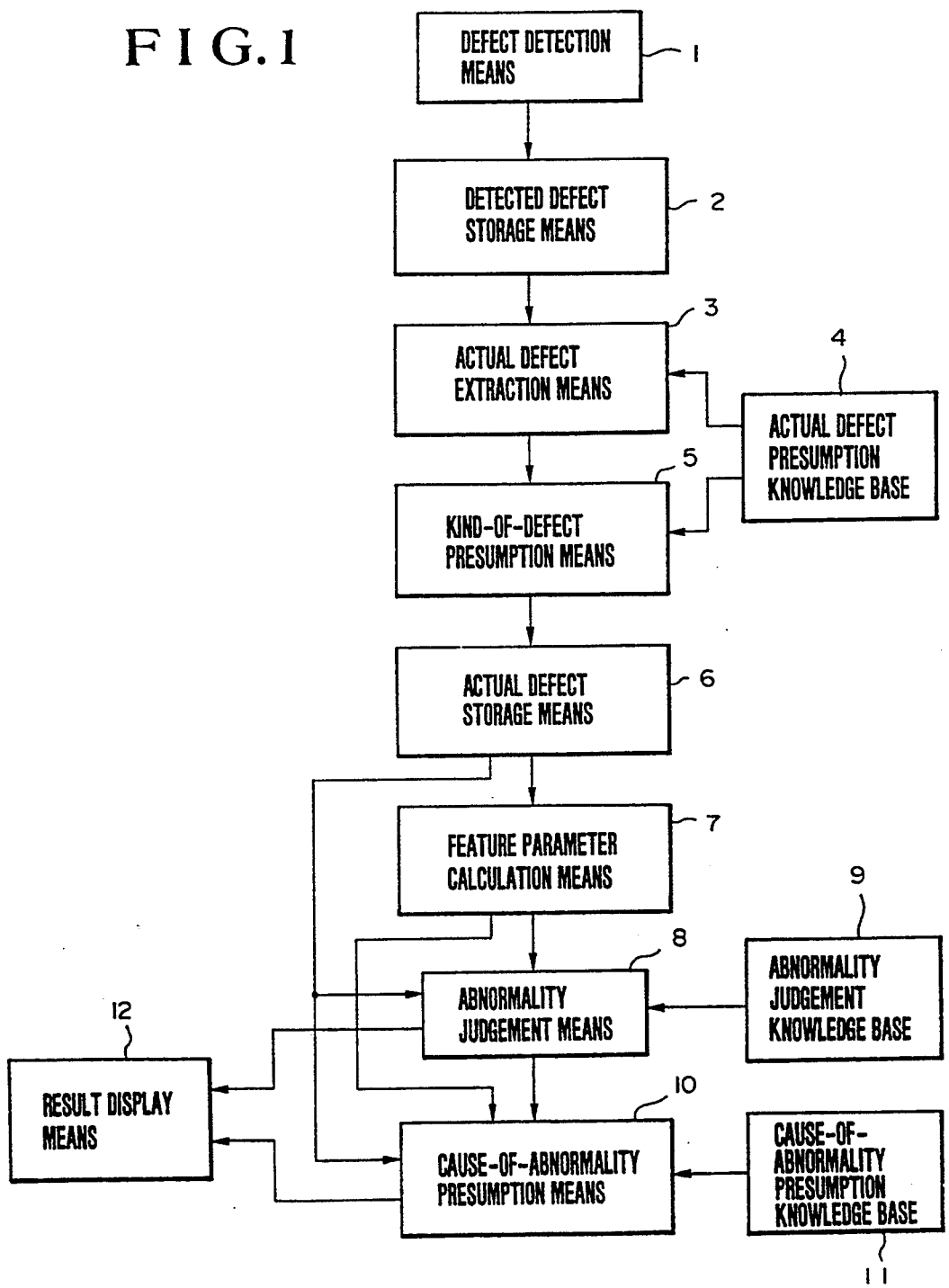
FIG. 1 is a block diagram showing an embodiment of an apparatus for visual inspection in accordance with the present invention which embodiment is used for carrying out a method of visual inspection in accordance with the present invention.

FIG. 1 is a block diagram showing an embodiment of an apparatus for visual inspection in accordance with the present invention, which embodiment is used for carrying out a method of visual inspection in accordance with the present invention. In FIG. 1, defect detection means 1 detects the position, kind and others of a defect on an object to be inspected, detected defect storage means 2 stores the position, kind and others of a detected defect, actual defect extraction means 3 calculates the distance between two detected defects from the positions of the two detected defects and for judging the two detected defects to be different portions of a single actual-defect when the distance between the two detected defects is less than a predetermined threshold value D, an actual defect inference knowledge base 4 stores a class-of-actual-defect inference rules necessary for inferring the class of an actual defect from the kind of each detected defect, and for storing the threshold value D (it is to be noted that the class-of-actual-defect inference rules is stored in the knowledge base 4 in the form of an if-then rule, that is, a rule composed of a condition part and a conclusion part), class-of-defect inference means 5 infers the kind of an actual defect from the class of each detected defect on the basis of the class-of-actual-defect inferring rules stored in the actual defect inference knowledge base 4, and actual defect storage means 6 stores the position, class and others of an actual defect. Each of the detected defect storage means 2 and the actual defect storage means 6 is formed of a semiconductor memory, a disk device, or others.

Further, in FIG. 1, feature parameter calculation means 7 obtains a feature parameter indicative of the variation of the number of actual defects with time and a feature parameter indicative of the two-dimensional distribution of actual defects, abnormality judgment knowledge base 9 stores abnormality judgment rules necessary for correlating a feature parameter with the presence of an abnormality in a manufacturing process (it is to be noted that the abnormality judgment rule is stored in the knowledge base 9 in the form of an if-then rule), abnormality judgment means judges the presence of an abnormality from a feature parameter on the basis of the abnormality judgment rule stored in the abnormality judgment knowledge base 9, cause-of-abnormality inference knowledge base 11 stores a cause-of-abnormality inference rule indicative of a causal relation between feature parameters and the cause of abnormality (it is to be noted that the cause-of-abnormality inference rules are stored in the knowledge base 11 in the form of an if-then rule), cause-of-abnormality inference means 10 for inferring the cause of abnormality from feature parameters on the basis of the cause-of-abnormality inference rule stored in the knowledge base 11, and result display means 12 displays the presence of abnormality, the degree of abnormality, an item considered as a probable cause of abnormality, and others.

Figure 2:
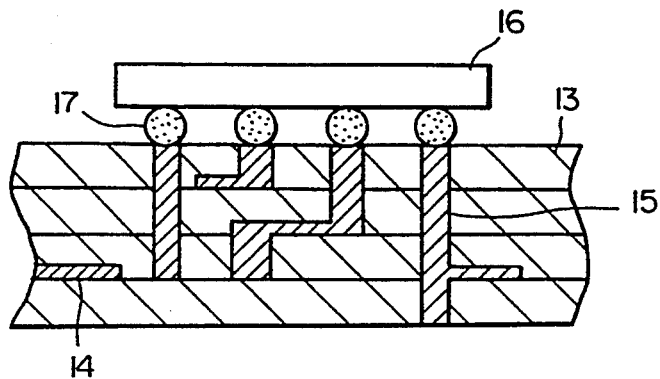
FIG. 2 is a sectional view showing a part of a ceramic circuit board whose appearance is inspected in the manufacturing process of the ceramic circuit board by the embodiment of FIG. 1.

FIG. 2 is a sectional view showing a part of a ceramic circuit board, the appearance of which is to be inspected in the manufacturing process of the circuit board by the present embodiment. In FIG. 2, the ceramic circuit board includes a multi-layered ceramic plate 13, a circuit pattern 14 formed on each layer of the plate 13 and made of tungsten, molybdenum, or others, a through-hole 15 for connecting circuit patterns, an electronic part 16 such as an IC chip, and a soldering joint 17.

Figure 3:
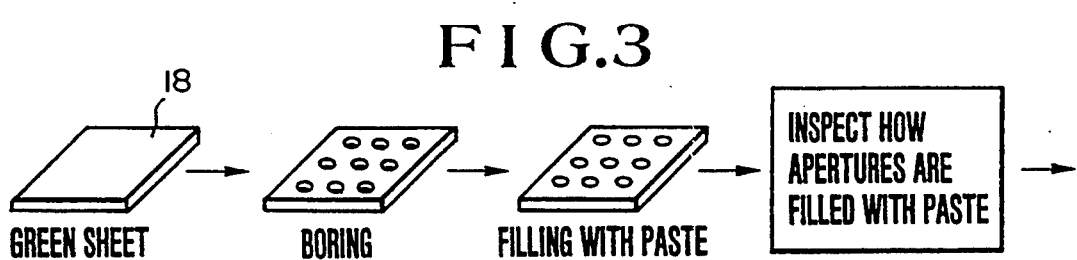
FIG. 3 is a schematic diagram for explaining some steps of a method of fabricating the ceramic circuit board of FIG. 2.

FIG. 3 is a schematic diagram for explaining some steps of a method of fabricating the ceramic circuit board of FIG. 2. Referring to FIG. 3, a sheet made of a ceramic material, that is, a green sheet 18 is cut so as to have a predetermined size. Then, through-holes are provided in the green sheet 18 by means of a boring tool such as a punch. Next, the through holes of the green sheet are filled with conductor paste by a screen printing method. Then, the present method inspects the quality of filling of each through-hole with the conductor paste.

Figure 4:
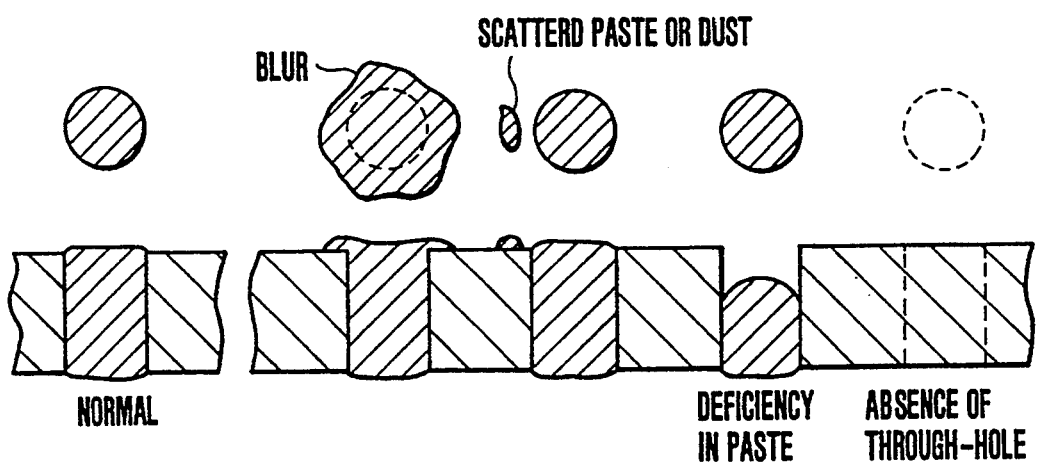
FIG. 4 shows plan and sectional views of a ceramic circuit board, illustrating various kinds of defects which are generated in filling through holes with conductor paste.

FIG. 4 includes plan and sectional views showing various kinds of defects which are generated in filling the through holes with the conductor paste. As shown in FIG. 4, the defects include a blur, scattered paste or dust, shortage, and absence of a through-hole. When the ceramic circuit board is formed by stacking a plurality of green sheets 18 with such defects, there is a possibility of generating a disconnection or short-circuit.

Figures 5, 6A, 6B:
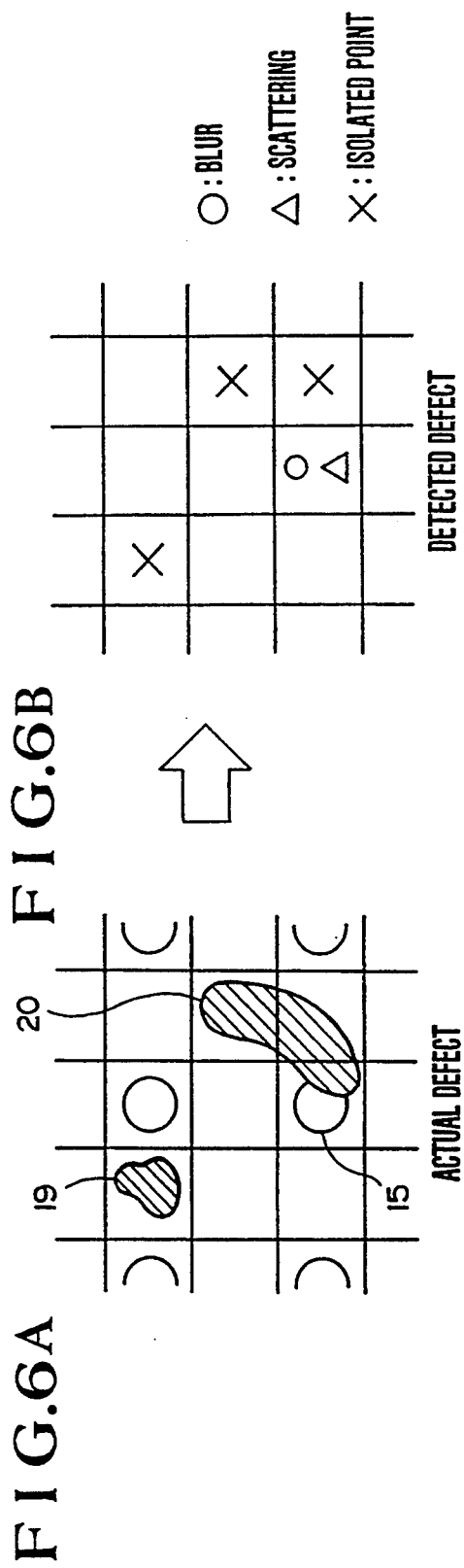
FIG. 5 is a table showing judgment criteria used in the defect detection means of FIG. 1.
FIG. 6A is a schematic diagram showing actual defects.
FIG. 6B is a schematic diagram showing various defects which are detected by inspecting the actual defects of FIG. 6A by the defect detection means.

FIG. 5 is a table showing defect judgment criteria which are used in the defect detection means 1 of FIG. 1. In the defect detection means 1, the image of green sheet 18 is taken from just above and from the upper left or right thereof to measure the area and circumference of conductor paste. Further, the number of defects and the position, kind and others of each defect are detected on the basis of the criteria of FIG. 5. In this case, the defect detection means 1 detects a defect at each unit area having the form of a regular square. In a case where a plurality of criteria are satisfied at one unit area, a plurality of defects are detected at the unit area.

The kind of defect is determined in the following manner. Expressing the area of conductor paste viewed from the upper left or right thereof and a reference value by $S_a$ and $S_o$, respectively, when the area $S_a$ is smaller than the reference value $S_o$ (the is, $S_a < S_o$), it is judged that the through hole is short of conductor paste. Further, expressing the area of conductor paste viewed from just above and another reference value by $S_b$ and $S_1$, respectively, when the area $S_b$ is smaller than the reference value $S_1$ (that is, $S_b < S_1$), it is judged that the through-hole is absent.

Expressing a further reference value by $S_2$, when the area $S_b$ is greater than the reference value $S_2$ (that is, $S_b > S_2$), it is judged that a blur is generated. Further, expressing the circumference of conductor paste viewed from just above and still another reference value by L and Th, respectively, when a ratio $S_b/L^2$ is smaller than the reference value Th (that is $S_b/L^2 < Th$), it is judged that scattering is generated. Finally, expressing a further reference value by $S_3$, when the area $S_b$ is greater than the reference value $S_3$ (that is, $S_b > S_3$), it is judged that an isolated point is present. Such defect detection means is disclosed in U.S. patent application Ser. No. 07/416,934, now U.S. Pat. No. 5,015,097.

FIG. 6A is a schematic diagram showing actual defects, and FIG. 6B is a schematic diagram showing defects which are detected by using the defect detection means 1 for the actual defects of FIG. 6A. As is apparent from FIGS. 6A and 6B, in a case where the actual defects include only fine dust 19, the number of actual defects agrees with the number of detected defects. On the other hand, in a case where the actual defects include large dust 20, the number of actual defects does not agree with the number of detected defects. Accordingly, in order to accuarately judge abnormalities in a manufacturing process, it is necessary to extract actual defects by means of the actual defect extraction means 3 of FIG. 1.

Figure 7:
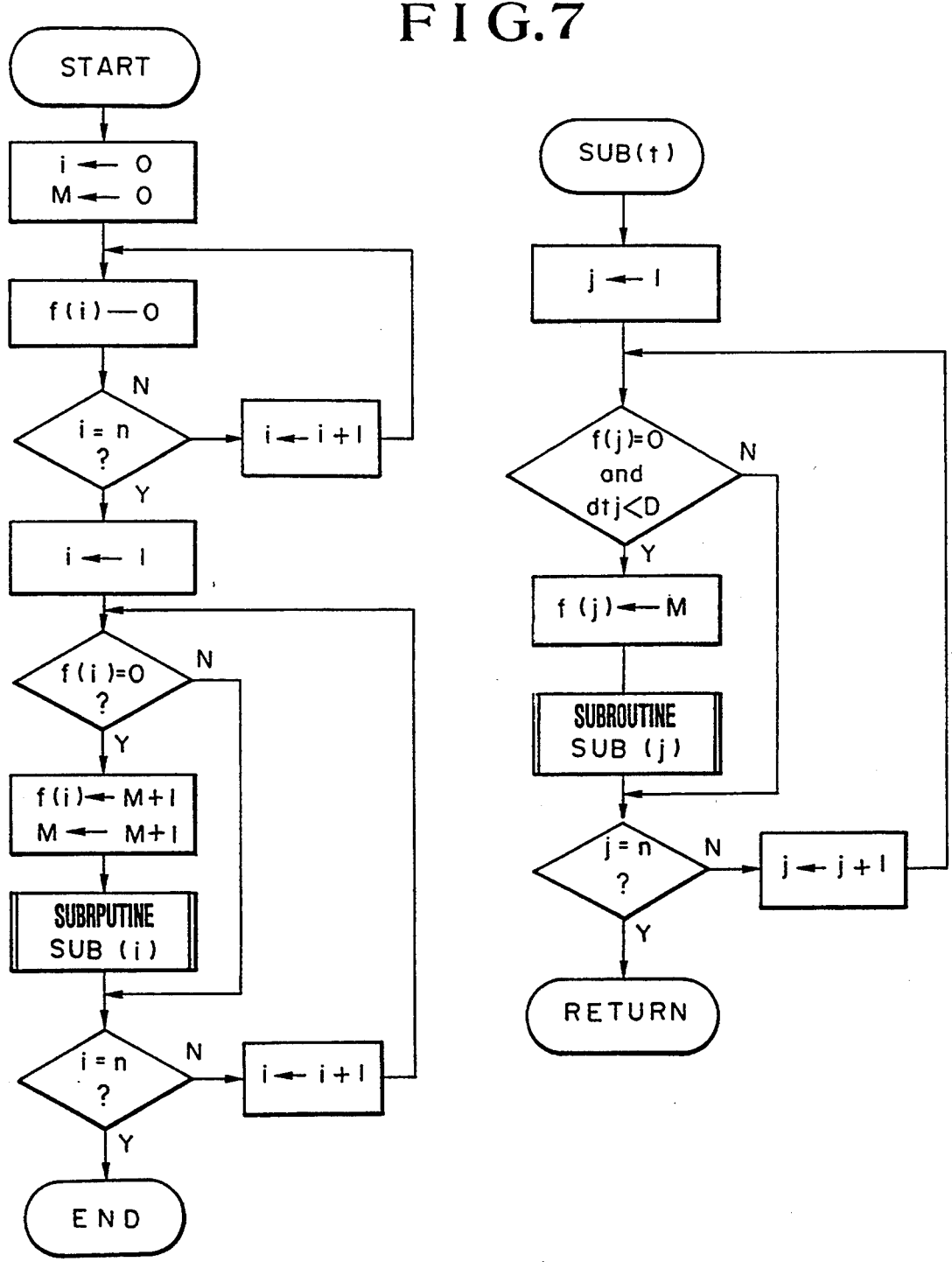
FIG. 7 is a flow chart showing an algorithm which is used in the actual defect extraction means of FIG. 1.

FIG. 7 is a flow chart which shows an algorithm used in the actual defect extraction means 3. In the actual defect extraction means 3, n detected defects $P_r$ (where r=1, - - -, n) are made to correspond to m actual defects $Q_s$ (where s=1, - - -, m), to extract actual defects. In more detail, an equation f(r)=s is introduced for making a detected defect $P_r$ correspond to an actual defect $Q_s$. Then, a detected defect $P_i$ which has not yet been made to correspond to any actual defect, and which is indicated by an equation f(i)=0, is made to correspond to an actual defect $Q_M$, as indicated by an equation f(i)=M. The distance $d_{ij}$ between the detected defect $P_i$ and each of the detected defects $P_j$ (where j=1, - - -, n, and f(j)=0) is the calculated. When the distance $d_{ij}$ is smaller than the threshold value D (that is, $d_{ij} < D$), it is judged that not only the detected defect $P_i$ but also the detected defect $P_j$ corresponds to the actual defect $Q_M$. That is, an equation f(j)=M is formed.

Next, the distance $d_{jk}$ between the detected defect $P_j$ and each of other detected defects $P_k$ (where k=1, - - -, n, and f(k)=0) is calculated, and detected defects satisfying a relation $d_{jk} < D$ are extracted. Such processing is carried out recursively.

FIG. 8 shows a case where formulas $d_{12} < D$, $d_{23} < D$, $d_{24} < D$, $d_{56} < D$, $d_{67} < D$ and $d_{47} > D$ are satisfied, by way of example in this case, it is inferred by the actual defect extraction means 3 that detected defects $P_1$, $P_2$, $P_3$ and $P_4$ belong to an actual defect $Q_1$ and detected defects $P_5$, $P_6$ and $P_7$ belong to another actual defect $Q_2$.

FIG. 9 is a table showing class-of-actual-defect inference rules which are stored in the actual defect inference knowledge base 4. For example, the class-of-actual-defect inference rules infer the kind of an actual defect in the following manner.

Referring to FIG. 9, the first rule is a rule indicating that if a blur defect, a scattering defect and an isolated point defect (shown in FIG. 5) are simultaneously detected, the class of the actual defect concerned is inferred to be the sticking of dust or paste on the green sheet.

The second rule of FIG. 8 is a rule indicating that if only a blur defect (shown in FIG. 5) is detected, the class of the actual defect concerned is inferred to be a blur of paste.

Further, the third rule is a rule indicating that if a blur defect and a shortage defect (shown in FIG. 5), are simultaneously detected, the class of the actual defect concerned is inferred to be the sticking of dust on the green sheet.

FIGS. 10A to 10C are graphs for explaining a method of obtaining a feature parameter which indicates the variation of the number of actual defects with time, by means of the feature parameter calculation means 7. As shown in FIG. 10A, actual defects produced on each green sheet 18 are classified into stationary defects, the number of which is always put within a predetermined range, and defects which occur suddenly. The former defects correspond to a stationary (static) state of a manufacturing process, and the latter defects correspond to sudden troubles in the manufacturing process. Hence, as shown in FIGS. 10B and 10C, the actual defects are separated into stationary defects corresponding to the stationary state and sudden defects corresponding to the sudden troubles. That is, when the number g(t) of defects at a time moment t (where t=1, 2, - - -, n) is given, a median h(t) is calculated which is given by the following equation:

h(t)=Median (g(t−1), g(t), g(t+1))

where t=2, 3, - - -, (n−1).

Next, a straight line $l_1$ is determined for the median h(t) by the least squares method. Then, the standard deviation $\sigma$ of the number of defects viewed from the straight line $l_1$ is calculated, and a straight line $l_2$ is drawn which is spaced apart from the straight line $l_1$ a distance of $3\sigma$ in an upward direction. When the number g(t) of defects exceeds the straight line $l_2$ at a particular time, it is judged that sudden defects occur at this time moment. After actual defects have been separated into stationary defects and sudden defects in the above manner, the inclination of the straight line $l_1$, that is, an increase rate b in the number of defects is calculated, to be used as a feature parameter indicative of the variation of the number of stationary defects with time.

Further, in the feature parameter calculation means 7, feature parameters for indicating the two-dimensional distribution of actual defects are determined in the following manner. When the number of actual defects produced on each green sheet 18 is expressed by N, and the position coordinates of each actual defect are expressed by $(x_i, y_i)$, the x- and y-coordinate factors $\bar{x}$ and $\bar{y}$ of the mean point of the two-dimensional distribution of actual defects and the x- and y-components $\sigma_x^2$ and $\sigma_y^2$ of the variance of the actual defects are calculated from the following equations (it is to be noted that the center of a region to be inspected, for example, the center of a green sheet 18, is used as the origin of a coordinate system):

$$\bar{x} = \sum_{i=1}^{N} x_i/N$$

$$\bar{y} = \sum_{i=1}^{N} y_i/N$$

-continued $$\sigma_x^2 = \sum_{i=1}^{N} (x_i - \bar{x})^2/N$$

$$\sigma_y^2 = \sum_{i=1}^{N} (y_i - \bar{y})^2/N$$

Further, in the feature parameter calculation means 7, the local density indicative of the number of defects in each unit area of a green sheet 18, which unit area has the form of a regular square, is calculated as a different feature parameter for indicating the two-dimensional distribution of actual defects. In a case where actual defects are concentrated in a local area, the local density at a specified unit area is increased.

FIG. 11 is a table showing abnormality judgment rules which are stored in the abnormality judgment knowledge base 9. In FIG. 11, abnormality values $X_1$, $X_2$ and $X_3$ lie in a range from 0 to 1, and the degree of abnormality increases as the abnormality value increases.

Referring to FIG. 11, the first rule is a rule indicating that if the square $(\bar{x}^2+\bar{y}^2)$ of the distance between the mean point $(\bar{x}, \bar{y})$ of the two-dimensional distribution of actual defects and the origin of the coordinate system used (for example, the center of a green sheet 18) is greater than a reference value $T_o$, it is judged that the actual defects are generated mainly on one side of the origin, and the degree of abnormality is expressed by an abnormality factor $X_1$. The abnormality factor $X_1$ may be a predetermined value, or may be determined in accordance with the difference between the value $(\bar{x}^2+\bar{y}^2)$ and the reference value $T_o$.

The second rule of FIG. 11 is a rule indicating that if the variance $\sigma^2 = \sigma_x^2 + \sigma_y^2$ of the distribution of actual defects calculated by the feature parameter calculation means is less than another reference value $T_1$, it is judged that the actual defects are localized, and the degree of abnormality is expressed by an abnormality factor $X_2$. Like the abnormality factor $X_1$, the abnormality factor $X_2$ is previously determined in a knowledge base.

Further, the third rule of FIG. 11 is a rule indicating that if the increase rate $\underline{b}$ in the number of defects calculated by the feature parameter calculation means 7 (that is, the inclination of the straight line $l_1$ shown in FIG. 10A) is greater than a reference value $T_2$, it is judged that the number of defects increases, and the degree of abnormality is expressed by an abnormality factor $X_3$. Like the abnormality factors $X_1$ and $X_2$, the abnormality value $X_3$ is previously determined in the knowledge base.

When, for example, the first and second rules of FIG. 11 are satisfied, it is judged by the abnormality judgment means 8 that actual defects are distributed mainly on one side of an origin, that is, have the abnormality factor $X_1$, and moreover the actual defects are localized, that is, have the abnormality factor $X_2$. In this case, a total abnormality factor X is given by the following equation:

$$X = X_1 + X_2 - X_1 \cdot X_2$$

As can be seen from the above, the presence of abnormality is judged by the abnormality judgment means 8.

FIG. 12 is a table showing cause-of-abnormality inference rules which are stored in the cause-of-abnormality inference knowledge base 11. In FIG. 12, certainty factors $Y_1$ and $Y_2$ indicate the degree of possibility of the cause of abnormality, and lie in a range from $-1$ (indicative of the complete negation of the possibility) to $+1$ (indicative of 100% possibility).

In the cause-of-abnormality inference means 10 of FIG. 1, it is checked on the basis of the feature parameters whether or not each of the cause-of-abnormality inference rules is satisfied. When it is judged that some cause-of-abnormality inference rules are satisfied, the cause of abnormality due to these rules inferred and the possibility of these causes are expressed by one of the certainty factors $Y_1$, $Y_2$, and so on.

Referring to FIG. 12, the first rule is a rule indicating that if stationary defects due to blurs occur in many places and moreover are uniformly distributed, it is supposed that the cause of abnormality is the inappropriate viscosity of the paste, and the degree of the possibility of the inappropriate viscosity is expressed by a certainty factor $Y_1$.

Further, the second rule of FIG. 12 is a rule indicating that if stationary defects due to the scattering of paste occur in many places and moreover are uniformly distributed, it is supposed that the cause of abnormality is the inappropriate viscosity of paste, and the degree of possibility of the inappropriate viscosity is expressed by a certainty factor $Y_2$.

Like the abnormality factors $X_1$, $X_2$ and $X_3$, the certainty factors $Y_1$ and $Y_2$ are previously set in a knowledge base.

In a case where a plurality of cause-of-abnormality inference rules are satisfied, and moreover the same cause of abnormality is supposed by the rules, for example, in a case where the first and second rules of FIG. 12 are satisfied, a total certainty factor Y is given by the following equations:

$$Y = Y_1 + Y_2 - Y_1 \cdot Y_2 \quad (Y_1 \geq 0, y_2 \geq 0)$$
$$Y = Y_1 + Y_2 + Y_1 \cdot Y_2 \quad (Y_1 \leq 0, Y_2 \leq 0)$$
$$Y = 0 \quad (Y_1 \cdot Y_2 = -1)$$
$$Y = \frac{Y_1 + Y_2}{1 - \min(|Y_1|, |Y_2|)} \quad (Y_1 \cdot Y_2 < 0)$$

Further, in a case where a plurality of causes contribute to abnormality, the cause of abnormality having the greatest one of the certainty factors $Y_1$, $Y_2$ and so on, is considered to be the most probable cause.

Next, explanation will be made of the operation of the embodiment of FIG. 1, that is, a method of visual inspection in accordance with the present invention. The number of defects produced in filling the through holes of each green sheet 18 with conductor paste, and the position, kind etc. of each of the defects are first detected by the defect detection means 1. Next, the number of detected defects and the position, kind etc. of each detected defect are stored in the detected defect storage means 2. When the number of detected defects on each of a predetermined number of green sheets and the position, class etc. of each of detected defects on each green sheet have been stored in the detected defect storage means 1, that is, when the inspection of defects for one manufacturing lot has been completed, actual defects on each green sheet are extracted by the actual defect extraction means 3 on the basis of the distance between two of the detected defects. Then, the class of an actual defect is inferred from the kind of each detected defect by the class-of-defect inference means 5 on the basis of class-of-actual-defect inference rules.

Next, the position, class etc. of an actual defect are stored in the actual defect storage means 6. Then, a feature parameter for indicating the variation of the number of actual defects with time and a feature parameter for indicating the two-dimensional distribution of actual defects are calculated from the position, class etc. of each actual defect by the feature parameter calculation means 7.

Then, the presence of an abnormality is judged from the feature parameters by the abnormality judgment means 8 on the basis of an abnormality judgment rule. Next, the cause of the abnormality is inferred from the feature parameters by the cause-of-abnormality inference means 10 on the basis of cause-of-abnormality inference rules. Finally, the presence of the abnormality, the degree of abnormality, and an item which is a probable cause of the abnormality are displayed by the result display means 12.

According to such visual inspection method and apparatus, actual defects are extracted. Accordingly, an abnormality in the manufacturing process of a ceramic circuit board and the cause of abnormality can be accurately judged, and the cause of the abnormality surely removed. As a result, the manufacturing yield and quality of the ceramic circuit board can be maintained or improved.

Further, the class-of-actual-defect inference rules in the actual defect inference knowledge base 4, the abnormality inference rules in the abnormality inference knowledge base 9, and the cause-of-abnormality inference rules in the cause-of-abnormality inference knowledge base 11 have the form of an if-then rule. Accordingly, the contents of knowledge used in the above method and apparatus are akin to human thinking. Moreover, items of the knowledge used are independent of each other, and thus it is easy to add or modify desired items.

Figure 13:
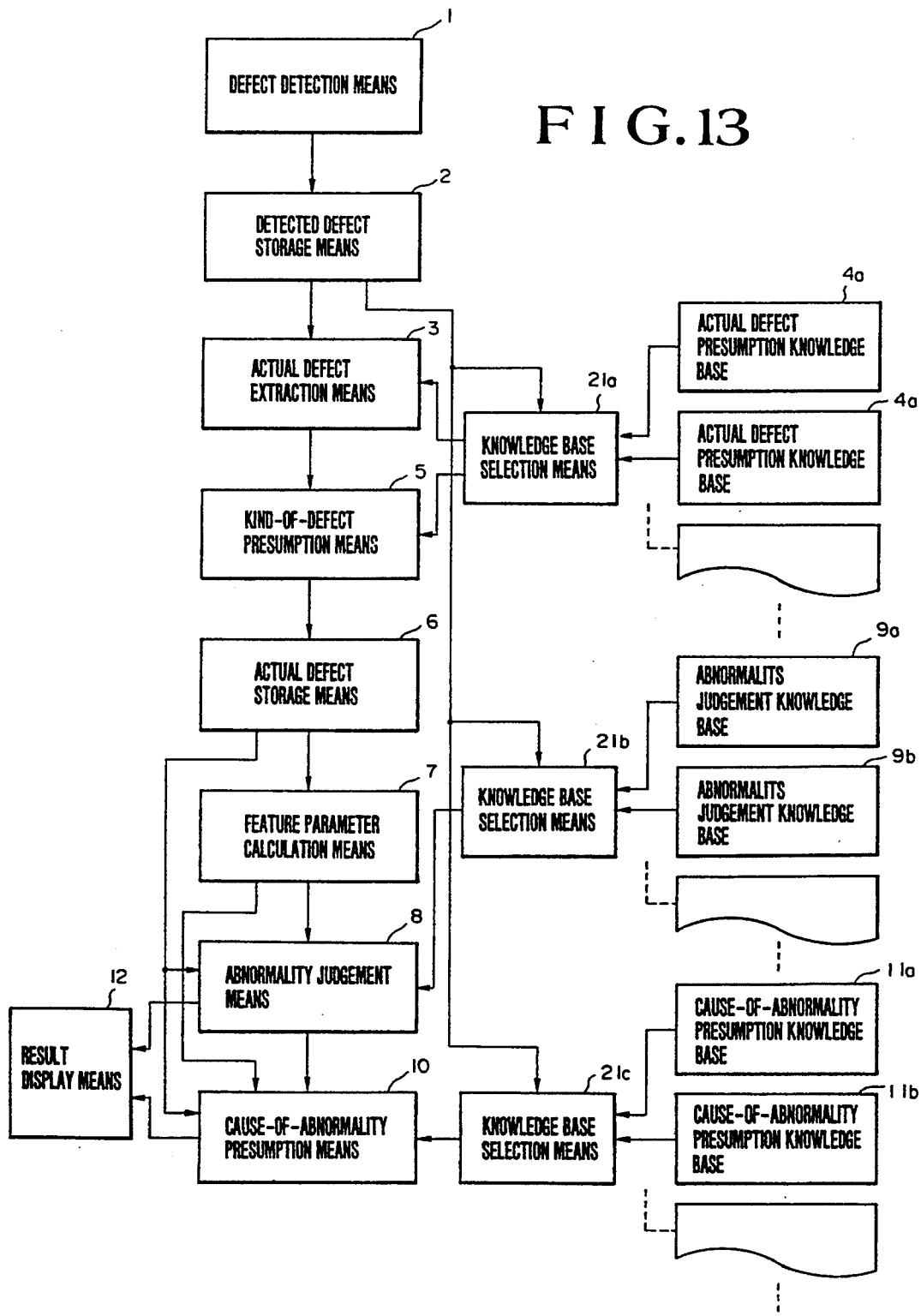
FIG. 13 is a block diagram showing another embodiment of an apparatus for visual inspection in accordance with the present invention, which embodiment is used for carrying out another method of visual inspection in accordance with the present invention.

FIG. 13 is a block diagram showing another embodiment of an apparatus for visual inspection in accordance with the present invention, which embodiment is used for carrying out another method of visual inspection in accordance with the present invention. In FIG. 13, reference numeral 21a designates knowledge base selection means for selecting one of the actual defect inference knowledge bases 4a, 4b and so on, 21b knowledge base selection means for selecting one of the abnormality judgment knowledge bases 9a, 9b and so on, and 21C knowledge base selection means for selecting one of the cause-of-abnormality inference knowledge bases 11a, 11b and so on.

In the embodiment of FIG. 13, each time one of the objects (for example, green sheets) which are to be inspected under different conditions is changed over to another object, an appropriate one of the actual defect inference knowledge bases 4a, 4b and so on, an appropriate one of the abnormality judgment knowledge bases 9a, 9b and so on, and an appropriate one of the cause-of-abnormality inference knowledge bases 11a, 11b and so on, are selected by the knowledge base selection means 21a, 21b and 21c, respectively. Thus, even when an inspecting condition is changed, inspection can be continuously carried out, provided that necessary knowledge bases are prepared.

Next, explanation will be made of a method of removing the cause of an abnormality in accordance with the present invention. The presence of the abnormality, the degree of the abnormality, and an item considered as a probable cause of abnormality are displayed on the display screen of the result display means 12 by the above-mentioned method of visual inspection. Then, the cause of the abnormality in the manufacturing process of a ceramic circuit board is removed on the basis of data on the display screen (that is, the presence of the abnormality, the degree of the abnormality and the item considered as a probable cause of the abnormality).

According to the above method of removing the cause of the abnormality, actual defects are extracted. Hence, an abnormality in the manufacturing process of a ceramic circuit board and the cause of the abnormality can be accurately judged. As a result, the cause of the abnormality is surely removed, and the manufacturing yield and quality of the ceramic circuit board are surely maintained or improved.

In the above embodiments, an explanation has been given of the inspection of the appearance in the manufacturing process of a ceramic circuit board. The present invention, however, is alo applicable to the inspection of the appearance in the manufacturing process of other articles.

As has been explained in the foregoing, according to an inventive method of visual inspection, an inventive apparatus for visual inspection, and an inventive method of removing the cause of an abnormality, an abnormality in a manufacturing process can be accurately judged, and thus the cause of the abnormality can be surely removed. Hence, the present invention has an advantage that the manufacturing yield and quality of an article can be surely maintained or improved.

We claim:

1. A computer-aided inspection system for inspecting the external appearance of circuit substrates during a manufacturing process, and for displaying an abnormality grade and a presumed cause of an abnormality occurring during the manufacturing process, comprising:

defect detection means for producing two-dimensional image signals, each representing the external appearance of one of said circuit substrates, and for detecting characteristics, including coordinates of defect candidates for each of said circuit substrates by comparing each of said two-dimensional image signals with a reference signal;

first storage means for storing said detected characteristics and coordinates of defect candidates over said plurality of circuit substrates manufactured by said manufacturing process;

actual defect extraction means for extracting actual defects from said defect candidates by grouping defect candidates having coordinates within a predetermined distance range from coordinates of candidates of defects stored in said first storage means for each of said plurality of circuit substrates manufactured by said manufacturing process, and for calculating locations for each of said extracted actual defects;

an actual defect presumption knowledge base for storing a presumption rule of kind of actual defect, the presumption rule being based on a plurality of correspondencies between a combination of said characteristics and actual kinds of factors of said actual defects;

presumption means for presuming a kind of factor for generating an actual defect from a combination of said stored characteristics of defect candidates stored in said first storage means, in accordance with said presumption rule;

second storage means for storing said calculated locations for each extracted actual defect extracted by said actual defect extraction means and for storing said presumed kind of factor for each actual defect presumed by said presumption means;

feature parameter calculation means for calculating a two-dimensional distribution of actual defects for said each kind of factor in at least one of said circuit substrates from said locations for actual defects stored in said second storage means, and for calculating a variation of the number of said actual defects for each kind of factor stored in said second storage means over said plurality of circuit substrates manufactured by said manufacturing process;

an abnormality judgment knowledge base for storing an abnormality judgment rule, the abnormality judgment rule being based on a two-dimensional distribution reference and a reference number variation for each kind of factor;

abnormality judgment means for determining an abnormality grade according to a partiality of a two-dimensional distribution obtained by comparing said calculated two-dimensional distribution for said each kind of factor with said two-dimensional distribution reference for each kind of factor, and according to an increase rate of number variation of actual defects obtained by comparing said calculated number variation of said actual defects for each kind of factor with said reference number variation for each kind of factor in accordance with said abnormality judgment rule stored in said abnormality judgment knowledge base;

a cause-of-abnormality presumption knowledge base for storing a presumption rule of cause of abnormality based on (1) a plurality of correspondencies between a combination of the two-dimensional distribution of said actual defects and the number variation of said actual defects for said each kind of factor, and (2) causes of abnormalities;

cause-of-abnormality presumption means for presuming a cause of the abnormality of said manufacturing process from a combination of said calculated two-dimensional distribution of actual defects and said calculated number variation of said actual defects for said each kind of factor stored in said second storage means, in accordance with said presumption rule of cause of abnormality; and display means for displaying said abnormality grade determined by said abnormality judgment means and said cause of abnormality of said manufacturing process presumed by said presumption means.

2. A computer-aided inspection system according to claim 1, wherein, when said abnormality judgment means has determined an abnormality, said cause-of-abnormality presumption means presumes a cause of said determined abnormality.

3. A computer-aided inspection system according to claim 1, wherein the abnormality grade and abnormality cause displayed by said display means relate to a process of printing a conductive paste in the through-holes of one of the circuit substrates.

4. A computer-aided inspection system according to claim 3, wherein said displayed abnormality grade and abnormality cause relate to one of an insufficiency of the conductive paste in said through-holes, excessive conductive paste in said through-holes and scattering of the conductive paste in said through-holes.

5. A computer-aided inspection system according to claim 1, wherein said feature parameter calculation means includes means for separating said actual defects into a stationary defect and a sudden defect, and means for separately calculating stationary defects and sudden defects from each other.

6. A computer-aided inspection method for inspecting the external appearance of circuit substrates during a process of manufacturing the circuit substrates, and for displaying an abnormality grade and a presumed cause of an abnormality occurring during the manufacturing process, comprising the steps of:

producing two-dimensional image signals, each representing the external appearance of one of said circuit substrates;

detecting characteristics, including coordinates of defect candidates, on each of said circuit substrates by comparing each of said two-dimensional image signals with a reference signal;

grouping defect candidates having coordinates neighboring each other within a predetermined distance range, and extracting the grouped defect candidates as actual defects from coordinates of the defect candidates stored in a first storage means for each of said circuit substrates over said plurality of circuit substrates;

calculating locations for each of said actual defects;

presuming a kind of defect-generating factor for each actual defect from a combination of said characteristics stored in said first storage means in accordance with a first presumption rule of kind of actual defect, the first presumption rule being based upon correspondencies between said characteristics and actual kind of defect-generating factors;

storing the kind of defect-generating factor for each actual defect presumed by said presuming step in a second storage means;

calculating a two-dimensional distribution of said actual defects for each kind of defect-generating factor in at least one of said circuit substrates from said stored locations for each actual defect in said second storage means;

finding a variation of the number of said actual defects for each stored kind of defect-generating factor over said plurality of circuit substrates;

comparing said calculated two-dimensional distribution of actual defects for each of said kind of defect-generating factors with a two-dimensional distribution reference;

determining an abnormality grade according to a partiality of two-dimensional distribution of defects obtained by said comparing step, and according to an increased rate of number variation of actual defects obtained by comparing said number variation with a reference number variation in accordance with an abnormality judgment rule;

presuming a cause of the abnormality of said manufacturing process from a combination of said calculated two-dimensional distribution of said actual defects and the number variation found by said finding step stored in said second storage means, in accordance with a second presumption rule of cause of abnormality, said second presumption rule being based on a plurality of correspondencies between (1) a combination of two-dimensional distribution of said actual defects and the number variation of said actual defects for each said kind of defect-generating factor, and (2) causes of an abnormality; and displaying the abnormality grade determined by said determining step and the cause of the abnormality of said manufacturing process presumed by said abnormality cause-presuming step.

7. A method according to claim 6, wherein said manufacturing process includes a step of printing a conductive paste in through-holes in one of the circuit substrates, and wherein the displaying step displays an abnormality grade and abnormality cause relating to a step of printing a conductive paste.

8. A method according to claim 7, wherein said displayed abnormality grade and abnormality cause relate to at least one of an insufficiency of the conductive paste in said through-holes, excessive conductive paste in said through-holes and scattering of the conductive paste in said through-holes.

9. A method according to claim 6, wherein the actual defects for which the step for calculating the number variation of actual defects is performed include a stationary defect and a sudden defect, and wherein the occurrences of said stationary defect and said sudden defect are calculated separately from each other.

10. A computer-aided inspection method according to claim 6, wherein, when an abnormality has been determined, said step for presuming a cause of the abnormality presumes a cause of the determined abnormality.

11. A computer-aided inspection method according to claim 6, wherein said two-dimensional distribution includes a mean point and a variance of the distribution.

* * * * *